United States Patent [19]
Allen et al.

[11] Patent Number: 5,567,489
[45] Date of Patent: Oct. 22, 1996

[54] MULTILAYER HALOGEN-FREE BARRIER FILM FOR OSTOMY AND TRANSDERMAL DRUG DELIVERY APPLICATIONS

[75] Inventors: Scott I. Allen, Newark; Michael Ferguson, Granville; Harvey Tung, Newark, all of Ohio

[73] Assignee: The Dow Chemical Company, Midland, Mich.

[21] Appl. No.: 216,905

[22] Filed: Mar. 23, 1994

Related U.S. Application Data

[63] Continuation-in-part of Ser. No. 121,634, Sep. 16, 1993, abandoned.

[51] Int. Cl.⁶ .................................................. B32B 27/08
[52] U.S. Cl. ...................... 428/34.1; 604/332; 604/338; 604/890.1; 604/891.1; 604/892.1; 424/443; 424/444; 424/449
[58] Field of Search ................ 428/34.1; 604/332, 604/338, 890.1, 891.1, 892.1; 424/443, 444, 449

[56] References Cited

U.S. PATENT DOCUMENTS

| | | | |
|---|---|---|---|
| 3,300,370 | 1/1967 | Epstein | 161/190 |
| 3,726,945 | 4/1973 | Bottenbruch et al. | 260/78 R |
| 3,997,383 | 12/1976 | Bieler et al. | 156/244 |
| 4,173,669 | 11/1979 | Ashida et al. | 428/35 |
| 4,230,830 | 10/1980 | Tanny et al. | 525/222 |
| 4,233,367 | 11/1980 | Ticknor et al. | 428/476.3 |
| 4,347,332 | 8/1982 | Odorzynski et al. | 524/169 |
| 4,427,825 | 1/1984 | Degrassi et al. | 525/56 |
| 4,457,960 | 7/1984 | Newsome | 428/35 |
| 4,461,808 | 7/1984 | Mollison | 428/475.8 |
| 4,468,427 | 8/1984 | Degrassi et al. | 428/226 |
| 4,557,780 | 12/1985 | Newsome et al. | 156/244.11 |
| 4,724,185 | 2/1988 | Shah | 428/339 |
| 4,795,781 | 1/1989 | Miyamoto et al. | 525/58 |
| 4,828,915 | 5/1989 | Schroeder et al. | 428/332 |
| 4,851,290 | 7/1989 | Vicik | 428/334 |
| 4,911,963 | 3/1990 | Luskig et al. | 428/36.91 |
| 4,952,628 | 8/1990 | Blatz | 525/58 |
| 5,053,259 | 10/1991 | Vicik | 428/36.91 |
| 5,077,109 | 12/1991 | Lustig et al. | 428/36.91 |

FOREIGN PATENT DOCUMENTS

| | | |
|---|---|---|
| 240886 | 10/1987 | European Pat. Off. . |
| 318025 | 5/1989 | European Pat. Off. . |
| 366802 | 5/1990 | European Pat. Off. . |
| 524775 | 1/1993 | European Pat. Off. . |
| 274387 | 12/1989 | Germany . |
| 93/11938 | 6/1993 | WIPO . |

OTHER PUBLICATIONS

William O'Kane et al, "The Effect of Annealing on the Structure and Properties of Isotactic Polypropylene Films", *J. Macromol. Sci.–Phys.*, B34(4), 427–458 (1995).
Brown et al, "The Structure of the Mesomorphic Phase of Quenched Isotactic Polypropylene", *Polymer*, vol. 35, No. 5, 1994, pp. 899, 907.
Document No. 290014 dated Oct. 1988 Research Disclosure.

Primary Examiner—Charles Nold

[57] ABSTRACT

An oxygen and moisture impermeable multilayer barrier film which is free of halogens and which may be produced by coextrusion or lamination techniques is provided. The film provides excellent adhesion between layers, has quietness, odor barrier, and softness characteristics, and provides a heat sealable surface for the fabrication of bags. The barrier film includes a halogen-free barrier layer and at least one heat sealable skin layer. The heat sealable skin layer includes either a thermoplastic polyurethane, a substantially linear copolymer of ethylene and an α-olefin having a density in the range of from about 0.87–0.92 gm/cc and from about 0.01 to 3 long chain branches/1000 carbon atoms along the polymer backbone, a homogeneously-branched linear polyolefin resin, or a blend of an ultra low density polyolefin resin with a copolymer of ethylene and vinyl acetate.

26 Claims, 2 Drawing Sheets

MULTILAYER HALOGEN-FREE BARRIER FILM FOR OSTOMY AND TRANSDERMAL DRUG DELIVERY APPLICATIONS

CROSS-REFERENCE TO RELATED APPLICATION

This application is a continuation-in-part of commonly-assigned U.S. patent application Ser. No. 08/121,634, filed Sep. 16, 1993 now abandoned.

BACKGROUND OF THE INVENTION

The present invention relates to an oxygen and moisture impermeable multilayer barrier film which is free of halogens, and to articles produced therefrom including ostomy bags or pouches and transdermal drug delivery systems.

Plastic film laminates having oxygen and moisture vapor barrier properties are desirable for current packaging requirements, as well as for use in medical applications such as the fabrication of ostomy bags and transdermal drug delivery systems. Where the films are to be used in ostomy applications, they must possess a unique combination of odor and moisture barrier properties as well as low noise, softness, heat or radio-frequency sealability, skin compatibility, and comfort. Such films have been provided in the past through the use of multi-ply film laminates where at least one of the plies is oxygen and moisture vapor impermeable. Typically, the barrier layer in these films comprises a halogen-containing polymer such as chlorinated polyethylene, plasticized polyvinyl chloride, or polyvinylidene chloride copolymers. Others have used multilayered barrier constructions such as ethylene vinyl acetate/polyvinylidene chloride/ethylene vinyl acetate combination films.

While such films have good barrier properties against oxygen, odor, and moisture, one major drawback has been the chlorine content of the films. Such chlorine-containing films are considered to create environmental hazards in their use and disposal in many countries. For example, German Patent No. DD 274,387 describes coextruded composite films for use in the manufacture of colostomy bags having a barrier layer of a copolymer of ethylene and vinyl alcohol and skin layers of a linear low density polyethylene.

Other known multilayer barrier films exist for varied uses including the packaging of meats where oxygen and moisture barrier properties are also important. For example, Lustig et al U.S. Pat. Nos. 5,077,109 and 4,911,963 teach multilayer films using Nylon as the barrier layer with linear low density or very low density polyethylenes as the skin layers. However, such films are taught to be biaxially oriented to improve puncture resistance, making them too noisy for use in ostomy applications.

Accordingly, the need still exists for multilayer barrier films which may be produced by conventional processes without the need for halogen-containing barrier layers and for films which are impermeable to moisture and oxygen, provide odor barrier, softness, and low noise properties, and which have a heat sealable surface for forming ostomy bags or the like.

SUMMARY OF THE INVENTION

The present invention meets that need by providing an oxygen and moisture impermeable multilayer barrier film which is free of halogens and which may be produced by coextrusion or lamination techniques. The film provides excellent adhesion between layers, has quietness, odor barrier, and softness characteristics, and provides a heat sealable surface for the fabrication of bags or the like.

According to one aspect of the present invention, an oxygen and moisture impermeable multilayer barrier film is provided which includes a halogen-free polymeric barrier layer coextruded with at least one heat sealable skin layer. To provide the desired softness characteristics, the heat sealable skin layer preferably has a 2% secant modulus of less than about 15,000 psi in both the machine (MD) and transverse(TD) directions. The heat sealable skin layer may comprise either a thermoplastic polyurethane, a substantially linear copolymer resin of ethylene and an α-olefin having a density in the range of from about 0.87–0.92 gm/cc and from about 0.01 to 3 long chain branches/1000 carbon atoms along the polymer backbone, a homogeneously-branched linear polyolefin resin, or a blend of an ultra low density polyolefin resin with a copolymer of ethylene and vinyl acetate. The barrier film exhibits a noise of less than about 85 dB when subjected to flexing through a 65° angle at 0.45 Hz, preferably exhibits a noise of less than about 83 dB when subjected to flexing through a 65° angle at 0.45 Hz, and most preferably exhibits a noise of less than about 81 dB when subjected to flexing through a 65° angle at 0.45 Hz. The barrier film has a heat seal strength of at least about 1.0 lb/inch of film width, and preferably greater than about 1.5 lb/inch of film width (ASTM 903 D).

By "oxygen impermeable", it is meant that the film has an oxygen transmission rate of equal to or less than about 400 $cc/m^2/day \cdot atm$. By "moisture impermeable", it is meant that the film has a water vapor transmission rate of equal to or less than about 30 $gm/m^2/day$. The term "heat sealable" is meant also to encompass radio-frequency sealing techniques.

The preferred halogen-free barrier layer material for the present invention comprises Nylon, either an amorphous Nylon resin, a crystalline Nylon resin such as Nylon 6 or Nylon 6/66 resin, or blends of amorphous and crystalline Nylons. Other suitable barrier materials for use in the present invention include copolymers of ethylene and vinyl alcohol (EVOH), blends of Nylon and EVOH, and multiple layers of these barrier materials. In a preferred embodiment of the invention, the heat sealable skin layers are included on both surfaces of the halogen-free barrier layer. As an aid in processing the film, the skin layer(s) may optionally contain from about 0.5–5% by weight of a slip additive/antiblocking agent package.

In one embodiment of the invention, the barrier layer may be coextruded with at least one heat sealable skin layer comprising either a thermoplastic polyurethane, a substantially linear copolymer of ethylene and an α-olefin having a density in the range of from about 0.87–0.92, or a blend of an ultra low density polyolefin resin with a copolymer of ethylene and vinyl acetate. Where the heat sealable skin layer comprises a thermoplastic polyurethane, it may be desirable to coextrude a layer of a chemically modified copolymer of ethylene and vinyl acetate between the barrier and skin layers to improve the adhesion between those layers. Where the heat sealable skin layer comprises a blend of an ultra low density polyolefin resin with a copolymer of ethylene and vinyl acetate, it may be desirable to coextrude a layer of a copolymer of ethylene and acrylic acid or a chemically modified copolymer of ethylene and vinyl acetate between the barrier and skin layers, again to improve the adhesion between those layers.

In a preferred embodiment of the invention, the barrier layer is coextruded between two heat sealable skin layers, where the skin layers comprise from about 70–90% by volume (thickness) of the film and the barrier layer comprises from about 10–30% by volume (thickness) of the film. The barrier and skin layer or layers may also be formed separately and then laminated together using suitable adhesive polymers, liquid adhesives, or hot melt adhesives. This construction may be used to form reusable ostomy bags or pouches. To form the bags, the film is folded over onto itself and the at least one skin layer is heat sealed along its edges.

In another embodiment of the invention, additional layers may be added to the barrier film to form a system for transdermal delivery of drugs. The system preferably comprises a backing layer of the barrier film which functions as a barrier to the drug system. An adhesive containing an active drug is preferably adhered to one surface of the film. Adjacent the adhesive is a controlled release membrane which is adapted to contact a patient's skin and to controllably release the drug. In another form of this embodiment, the backing layer may form a reservoir for containing the active drug with the controlled release membrane covering the opening of the reservoir to control the diffusion of the drug into a patient's skin. A peripheral or overall adhesive may be used to adhere the transdermal delivery system to a patient's skin. Preferably, a release liner overlies the adhesive and membrane to protect the construction prior to use.

Accordingly, it is a feature of the present invention to provide an oxygen and moisture impermeable multilayer halogen-free barrier film which may be produced using coextrusion or lamination processes. Further features of the invention include odor barrier, softness, and low noise properties. Additionally, a heat sealable surface for use in forming bags and pouches is provided. These, and other features and advantages of the present invention will become apparent from the following detailed description, the accompanying drawings, and the appended claims.

DETAILED DESCRIPTION OF THE PREFERRED EMBODIMENTS

In one embodiment, the multilayer barrier film of the present invention may be produced using standard extrusion techniques such as feedblock coextrusion, multi-manifold die coextrusion, or combinations of the two. The volume (thickness) of each individual layer may be controlled as it is extruded. Thus, the overall thickness of the multilayer structure may be controlled. Alternatively, the individual layers may be formed separately and laminated together using suitable adhesive bonding layers.

The polymers in the films are not intentionally stretched or oriented other than as a natural consequence of their manufacture to preserve their low noise characteristics. For example, films produced by a blown process will inherently have some orientation in both the machine (MD) and transverse (TD) directions, while cast films will remain unoriented in the transverse direction. Generally, the less orientation which is introduced into the films, the less noisy they will be. The multilayer barrier films of the present invention exhibit a noise of less than about 85 dB when subjected to flexing through a 65° angle at 0.45 Hz, preferably exhibit a noise of less than about 83 dB when subjected to flexing through a 65° angle at 0.45 Hz, and most preferably exhibit a noise of less than about 81 dB when subjected to flexing through a 65° angle at 0.45 Hz.

Additionally, to provide the desired softness characteristics, the heat sealable skin layer preferably has a 2% secant modulus of less than about 15,000 psi in both the machine (MD) and transverse (TD) directions. 2% secant modulus is a measure of the stiffness or softness of a film. We have found that the lower the value for 2% secant modulus for the heat sealable skin layer, the softer the resulting film will be. Generally, it is desirable for the 2% secant modulus of the film to be as low as possible and yet still remain processable by conventional equipment. For the overall multilayer film, it is preferable that the 2% secant modulus be 30,000 psi or below. The resulting multilayer films possess low oxygen and vapor transmission rates, as well as having the odor barrier, softness, and low noise properties needed for ostomy applications.

Figure 1:
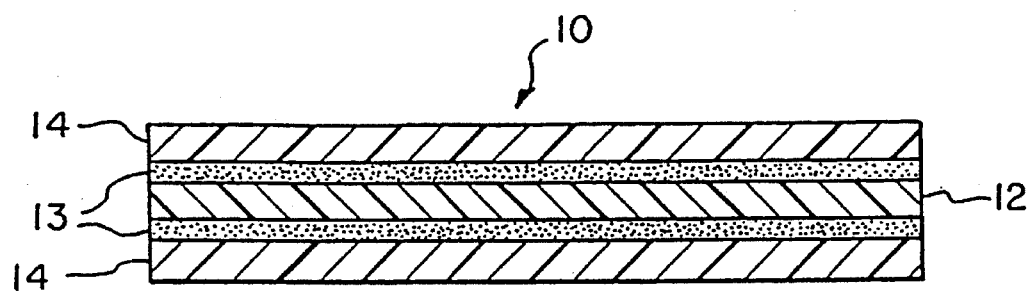
FIG. 1 is a schematic cross-section of the multilayer barrier film of the present invention.

Referring now to FIG. 1, an oxygen and moisture impermeable multilayer barrier film 10 is illustrated. The film 10 includes a halogen-free barrier layer 12 which may be either an amorphous Nylon, a crystalline Nylon, blends of amorphous and crystalline Nylons, a copolymer of ethylene and vinyl alcohol (EVOH), blends of EVOH and Nylons, and multiple layers of such barrier materials. A preferred Nylon is an amorphous Nylon Selar® PA3426, commercially available from E.I. du Pont de Nemours Co., Inc. Other suitable commercially available Nylons include Capton® 1539, a Nylon 6/66 resin from Allied Corporation and Capron® 100F, also available from Allied Corporation. An amorphous Nylon is preferred as we have found the amorphous Nylons to possess superior odor barrier properties.

As shown, the halogen-free barrier layer is preferably coextruded with or laminated to two heat sealable thermoplastic skin layers 14 with adhesive layers 13 sandwiched therebetween. The skin layers comprise either a thermoplastic polyurethane, a substantially linear copolymer resin of ethylene and an α-olefin having a density in the range of from about 0.87–0.92 gm/cc and from about 0.01 to 3 long chain branches/1000 carbon atoms along the polymer backbone, a homogeneously-branched linear polyolefin resin, or a blend of an ultra low density polyolefin resin with a copolymer of ethylene and vinyl acetate. Suitable thermoplastic polyurethanes include those based on the reaction of a polyisocyanate (aromatic or aliphatic) with polyester, polyether, or polycaprolactone polyols. Chain extenders such as diols and diamines may also be used in the reaction. Such thermoplastic polyurethanes are commercially available from E.I. du Pont de Nemours Co., Inc. under the trademark Hytrel®, from the B.F. Goodrich Co. under the trademark Estane®, and from The Dow Chemical Company under the trademark Pellathane®. A preferred thermoplastic polyurethane composition is Hytrel® 4056.

To aid in processing of the thermoplastic polyurethane skin layers, the skin layers may contain from 0 to 10% by weight of a copolymer of ethylene and vinyl acetate, and more preferably, from 0.5–5% by weight. In addition, the skin layers may contain from about 0.5–6% by weight of a slip additive such as 16SFI, commercially available from Akzo Chemical Inc. The thermoplastic polyurethane skin layers used in the present invention typically will provide a heat seal strength in the range of from about 7 to 9 lb/inch of film width (ASTM 903 D).

It may also be desirable to coextrude or otherwise position an adhesive layer 13 of a copolymer of ethylene and vinyl acetate between the barrier and thermoplastic polyurethane skin layers to improve the adhesion between those layers. A preferred adhesive is Plexar® 3342, commercially available from Quantum Chemical Corp.

Suitable homogeneously-branched linear polyolefin resins are commercially available from Exxon Corporation under the trademark Exact® or from Mitsui Chemical Co. under the trademark Tafmer®.

A suitable substantially linear copolymer resin of ethylene and an α-olefin is taught in commonly-assigned published PCT application PCT/US92/08812, published Apr. 27, 1993, the disclosure of which is hereby incorporated by reference. These copolymer resins are commercially available from The Dow Chemical Company as polymer resins made using Insite™ constrained geometry catalyst technology (CGCT). The constrained geometry catalysts are described in commonly-assigned copending U.S. application Ser. Nos. 545,403, filed Jul. 3, 1990, 758,654, filed Sep. 12, 1991, 758,660, filed Sep. 12, 1991, and 720,041, filed Jun. 24, 1991. The catalysts may be generally characterized as comprising a metal coordination complex of a metal of Groups 3–10 or the Lanthanide series of the Periodic Table of Elements and a delocalized n-bonded moiety substituted with a constrain-inducing moiety.

Such substantially linear copolymers have the strength and toughness of linear low density polyethylene (LLDPE) but with processability similar to highly branched low density polyethylene (LDPE). Thus, the polymers have processing indices (PI's) less than or equal to 70% of those of a comparable linear olefin polymer and a critical shear rate at onset of surface melt fracture of at least 50% greater than the critical shear rate at onset of surface melt fracture of a traditional linear olefin polymer at about the same $I_2$ and $M_w/M_n$, where $I_2$ is the melt index measured according to ASTM D-1238, Condition 190° C./2.16 kg (formerly known as "Condition E"), $M_w$ is the weight average molecular weight, and $M_n$ is the number average molecular weight of the polymer. The substantially linear copolymers will have from about 0.01 to 3 long chain branches/1000 carbon atoms along the polymer backbone, where long chains are defined as a chain length of at least 6 carbon atoms.

Moreover, these substantially linear copolymers have desirable quietness for use in ostomy applications. Such substantially linear ethylene/α-olefin copolymers typically will provide a heat seal strength in the range of from about 2 to 3 lb/inch of film width (ASTM 903 D). Thus, these substantially linear copolymers are preferred for use in the present invention because they possess a unique combination of processability, quietness, and heat seal strength.

A suitable blend of an ultra low density polyolefin resin with a copolymer of ethylene and vinyl acetate for use as a heat sealable skin layer in the present invention includes from about 5–95% by weight of ultra low density polyolefin resin blended with from about 95–5% by weight copolymer of ethylene and vinyl acetate. Preferably, from about 0.5–6% by weight of a slip additive/antiblocking agent package is also included in the blend. A preferred blend of components contains 55% of a copolymer of ethylene and vinyl acetate, 40% ultra low density polyolefin resin, and 5% slip additive.

A suitable class of ultra low density polyolefin resins are Attane® resins, commercially available from The Dow Chemical Company. A suitable class of copolymers of ethylene and vinyl acetate are Elvax® resins, commercially available from E.I. du Pont de Nemours Co., Inc. The slip additive may be any of a number of well known materials commercially available from a variety of sources.

It also may be desirable to coextrude or otherwise position an adhesive tie layer 13 of a copolymer of ethylene and acrylic acid between the barrier and blend of ultra low density polyolefin resin and copolymer of ethylene and vinyl acetate skin layers, again to improve the adhesion between those layers. A preferred adhesive is Primacot® 1410XT, a copolymer of ethylene and acrylic acid which is commercially available from The Dow Chemical Company.

The barrier film 10 may be used to form a reusable ostomy bag or pouch by folding the film and heat sealing either the thermoplastic polyurethane, substantially linear ethylene/α-olefin copolymer, or blend of ultra low density polyolefin resin and copolymer of ethylene and vinyl acetate skin layers to each other. Preferably, the bag will have an oxygen permeability of less than about 400 $cc/m^2$/day·atm (26 cc/100 $in^2$/day·atm). The barrier film 10 may have a total thickness of between about 35 and 100 micrometers, with the barrier layer 12 making up from about 10 to 30% of the total thickness (volume) of the film. The skin layers (and adhesive layers, if needed) will typically make up about 70 to 90% of the total thickness (volume) of the film.

The multilayer barrier films of the present invention may also be formed by lamination techniques using suitable adhesives. For example, the barrier and skin layer or layers may be formed separately and then laminated together using adhesive polymers, liquid adhesives, or hot melt adhesives. Suitable adhesive polymers to bond the barrier and skin layers include, but are not limited to, ethylenically unsaturated copolymers of vinyl acetate, ethyl acrylate, ethyl methacrylate, methyl acrylic acid, acrylic acid, and carbon monoxide. Other examples include ionomers of ethylene and methyl acrylic acid or acrylic acid and grafted anhydride copolymers. Suitable liquid or hot melt adhesives include, but are not limited to, adhesives based on urethanes, copolyesters, and copolymers of amide acrylates.

Figure 2:
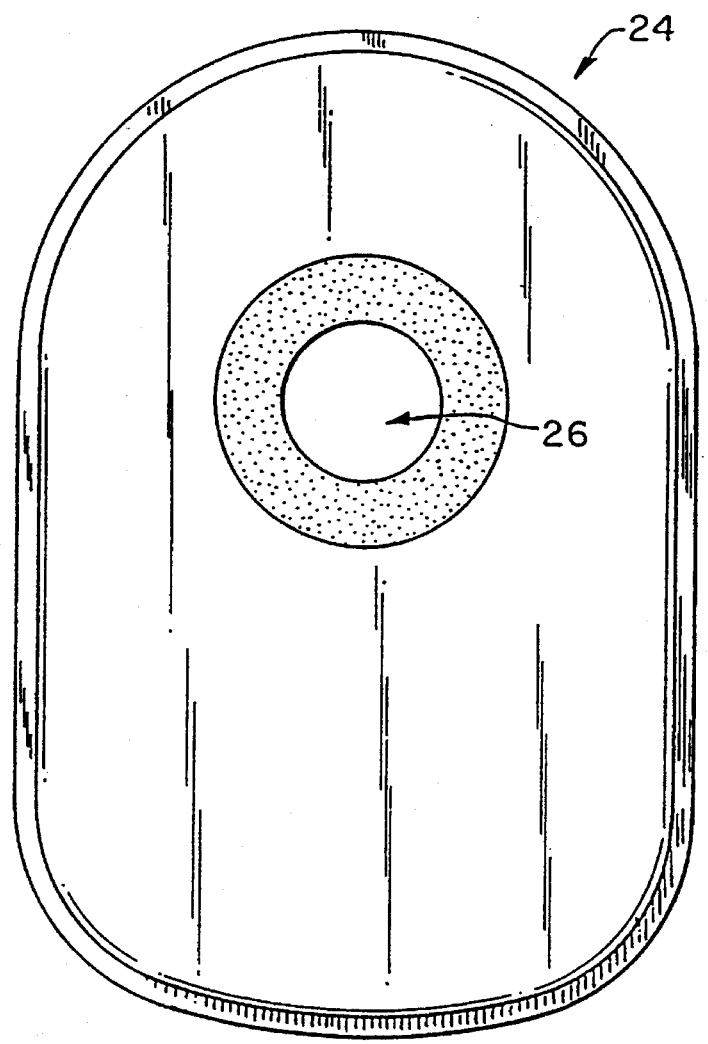
FIG. 2 is a front elevational view of an ostomy bag or pouch formed from the multilayer barrier film of FIG. 1 of the present invention.

FIG. 2 illustrates a typical reusable ostomy bag 24 including an opening 26 formed from the multilayer barrier films of FIG. 1. The bag may be formed by folding and heat sealing the edges of multilayer film 10. The film is preferably folded and sealed such that one heat sealable skin layer provides the inner surface of the bag or pouch 24. The halogen-free barrier film of the present invention provides softness and quietness features which are desirable for ostomy applications, as well as moisture resistance and odor and oxygen barrier properties. As will be appreciated by those skilled in the art, the barrier films of the present invention may also find use in other packaging applications where moisture and oxygen barrier properties are required.

Figure 3:
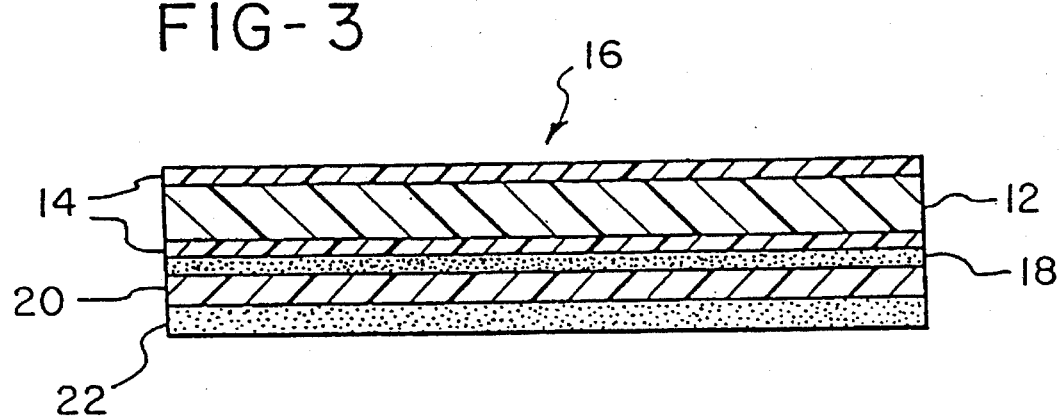
FIG. 3 is a schematic cross-section of one embodiment of a transdermal drug delivery system in accordance with the present invention.

FIG. 3 illustrates another embodiment of the invention in which additional layers are included with the barrier film to form a system 16 for transdermal delivery of drugs. In its simplest form, the barrier layer 12 and skin layers 14 of the film serve as a backing film that is a barrier to the drug system. The barrier film further includes an adhesive layer 18 containing an active drug blended in a matrix therein adhered to one surface of the film. The adhesive which is selected should be compatible with the active drug and permeable to the drug. There are many active drugs which can be administered to a patient in this manner including, for example, estrogen, nitroglycerin, nicotine, and scopolamine. In theory, almost any drug may be administered in this manner.

A controlled release membrane 20 adapted to contact a patient's skin and to controllably release the drug overlies adhesive layer 18. An additional adhesive layer 22, which may be applied peripherally or over the entire surface of membrane 20, may also be present to secure the transdermal delivery system 16 to a patient's skin. The adhesives used in the practice of this embodiment of the invention should be medical grade adhesives such as silicone, acrylic, or vinyl acetate adhesives. Generally, in this embodiment, the system 16 will be sealed in a package or secured to a second barrier film which is removed prior to use.

Figure 4:
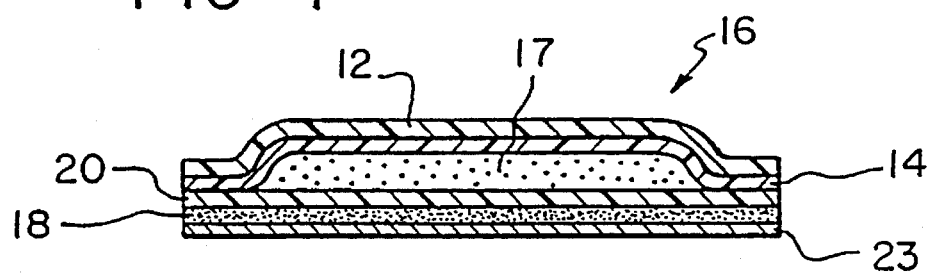
FIG. 4 is a schematic cross-section of another embodiment of a transdermal drug delivery system in accordance with the present invention.

FIG. 4 illustrates an alternative form of a transdermal drug delivery system 16 in accordance with the present invention. Barrier layer 12 and skin layer 14 form a barrier film which is formed into a reservoir to contain active drug 17 therein. The opening to the reservoir is covered by a controlled release membrane 20. An adhesive 18, which may either be peripherally applied or applied over the entire area of membrane 20, acts to secure system 16 to a patient's skin. Again, the adhesive which is selected should be compatible with the active drug and permeable to the drug. Preferably, a release liner 23 or the like covers and protects the adhesive 18 and membrane 20 prior to use.

In order that the invention may be more readily understood, reference is made to the following examples, which are intended to be illustrative of the invention, but are not intended to be limiting in scope.

EXAMPLE 1

A five-layer barrier film was produced in accordance with the present invention and included a core barrier layer, two outer skin layers, and two intermediate adhesive tie layers joining the core and outer skin layers together. The layers were coextruded using conventional techniques. The core barrier layer was Capron® 1539, a Nylon 6/66 resin commercially available from Allied Corporation. The two outer skin layers comprised a blend of 50% Elvax® 3165 (E.I. du Pont de Nemours and Co., Inc.), 40% Attane® 4202 (The Dow Chemical Company), and 5% of a slip additive such as CN4420. The two intermediate tie layers were Primacor® 1410XT (The Dow Chemical Company).

The resulting five layer halogen-free barrier film had a thickness of approximately 3.0 mils and an ultimate tensile strength (ASTM D-882) of 4,404 (MD) and 3,737 (TD) psi, respectively. The film had an oxygen transmission rate (ASTM D-3985) of 22.2 cc/100 in$^2$/day·atm and a water vapor transmission rate (Permatran W) of 0.94 gm/100$^2$/day. The film also had a 2% secant modulus (ASTM method D-882 using an Instron tensile tester) of 15,170 psi (MD) and 14,640 psi (TD).

The five layer film was tested for quietness by forming a 4"×4" piece of the film having a 3.0 mil thickness into a cylinder and flexing the film through an angle of 65° at a frequency of 0.45 Hz and measuring the sound level in decibels (dB). Over several tests, the measured noise varied from 78.7 to 82.7 dB.

EXAMPLE 2

A five-layer barrier film was produced in accordance with the present invention and included a core barrier layer, two outer skin layers, and two intermediate adhesive tie layers joining the core and outer skin layers together. The layers were coextruded using conventional techniques. The core barrier layer was Capron® 100F, a Nylon 6 resin commercially available from Allied Corporation. The two outer skin layers comprised Hytrel® 4056, a thermoplastic polyurethane from E.I. du Pont de Nemours and Co., Inc. and 6% of a slip additive 16SFI (Akzo Chemical Inc.). The two intermediate adhesive tie layers were Plexar® 3342 (Quantum Chemical Corp.).

The resulting five layer halogen-free barrier film had a thickness of approximately 3.0 mils and an ultimate tensile strength (ASTM D-882) of 4,079 (MD) and 3,262 (TD) psi, respectively. The film had an oxygen transmission rate (ASTM D-3985) of 18.8 cc/100 in$^2$/day·atm and a water vapor transmission rate (Permatran W) of 1.59 gm/100$^2$/day. The film also had a 2% secant modulus (ASTM method D-882 using an Instron tensile tester) of 18,070 psi (MD) and 17,490 psi (TD).

The five layer film was tested for quietness by forming a 4"×4" piece of the film having a 3.0 mil thickness into a cylinder and flexing the film through an angle of 65° at a frequency of 0.45 Hz and measuring the sound level in decibels (dB). Over several tests, the measured noise varied from 82.0 to 84.0 dB.

EXAMPLE 3

A five-layer barrier film was produced in accordance with the present invention and included a core barrier layer, two outer skin layers, and two intermediate adhesive tie layers joining the core and outer skin layers together. The layers were coextruded using conventional techniques. The core barrier layer was an amorphous Nylon resin, Selar® PA3426 commercially available from E.I. du Pont de Nemours Co., Inc. The two outer skin layers comprised a blend of 55% Elvax® 3165D (E.I. du Pont de Nemours and Co., Inc.), 40% Attane® 4202 (The Dow Chemical Company), and 5% of a slip additive such as CN4420. The two intermediate adhesive tie layers were Plexar® 3342 (Quantum Chemical Corp.).

The resulting five layer halogen-free barrier film had a thickness of approximately 4.0 mils and an ultimate tensile strength (ASTM D-882) of 2,300 (MD) and 1,800 (TD) psi, respectively. The film had an oxygen transmission rate (ASTM D-3985) of 10.0 cc/100 in$^2$/day·atm and a water vapor transmission rate (Permatran W) of 0.703 gm/100 in$^2$/day. The film also had a 2% secant modulus (ASTM method D-882 using an Instron tensile tester) of 27,000 psi (MD) and 25,000 psi (TD).

EXAMPLE 4

To demonstrate the quietness of the skin layers used in the multilayer barrier films of the present invention, a number of monolayer films were prepared using a cast film process. Monolayer films of a thermoplastic polyurethane and a substantially linear ethylene/α-olefin copolymer of the present invention were cast and tested for comparison purposes against prior art chlorinated polyethylene and homogeneously-branched polyethylene films.

The five layer films were tested for quietness by forming a 4"×4" piece of the film into a cylinder and flexing the film through an angle of 65° at a frequency of 0.45 Hz and measuring the sound level in decibels (dB). Data are reported in Table 1 below. The measured noise was comparable in quietness to other films in commercial use.

TABLE 1

| Sample # | Polymer Resin | Noise (dB) | 2% secant Modulus MD (psi) | 2% secant Modulus TD (psi) |
|---|---|---|---|---|
| 1 | Chlorinated polyethylene | 80.0 | 4,000 | 4,000 |
| 2 | Ultra low density polyethylene (Dow Attane ® 4202, 0.912 g/cc, 3.2 MI) | 83.5 | 12,500 | 12,500 |
| 3 | CGCT linear ethylene/α-olefin copolymer (0.909 g/cc, 3.2 MI) | 83.5 | 12,000 | 12,000 |
| 4 | Blend of 33% CGCT substantially linear ethylene/α-olefin copolymer (0.871 g/cc, 1.0 MI) 67% CGCT substantially linear ethylene/α-olefin copolymer (0.8995 g/cc, 2.7 MI) and 6% CN315 | 80.0 | 5,000 | 5,500 |
| 5 | Blend of 50% CGCT substantially linear ethylene/α-olefin copolymer (0.871 g/cc, 1.0 MI) 50% CGCT substantially linear ethylene/α-olefin copolymer (0.8995 g/cc, 2.7 MI) and 6% CN315 | 81.0 | 4,000 | 4,500 |
| 6 | Blend of 67% CGCT substantially linear ethylene/α-olefin copolymer (0.871 g/cc, 1.0 MI) 33% CGCT substantially linear ethylene/α-olefin copolymer (0.8995 g/cc, 2.7 MI) and 6% CN315 | 80.0 | 3,000 | 3,500 |
| 7 | Blend of 89% CGCT substantially linear ethylene/α-olefin copolymer (0.871 g/cc, 1.0 MI) 11% CGCT substantially linear ethylene/α-olefin copolymer (0.8995 g/cc, 2.7 MI) and 6% CN315 | 81.0 | 2,500 | 3,000 |
| 8 | CGCT substantially linear ethylene/α-olefin copolymer (0.8995 g/cc, 2.7 MI) and 6% CN315 | 82.0 | 7,500 | 7,720 |
| 9 | Tafmer ® 4090 (Mitsui) (0.89 g/cc, 3.6 MI) and 6% CN315 | 83.0 | 6,670 | 7,080 |
| 10 | Tafmer ® 4085 (Mitsui) (0.88 g/cc, 3.6 MI) and 6% CN315 | 81.0 | 4,600 | 4,920 |
| 11 | Tafmer ® 4080 (Mitsui) (0.87 g/cc, 1.1 MI) and 6% CN315 | 79.0 | 3,060 | 2,900 |
| 12 | Thermoplastic polyurethane (Dow Pellathane ® 2355-95AE) | 81.5 | 6,900 | 7,000 |
| 13 | Thermoplastic polyurethane (Dow Pellathane ® 2363-90AE) | 79.5 | 4,900 | 5,000 |

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. An oxygen and moisture impermeable multilayer barrier film comprising a halogen-free polymeric barrier layer and at least one heat sealable skin layer, said skin layer comprising a thermoplastic polymer having a 2% secant modulus of less than about 15,000 psi in both the machine and transverse directions, said barrier film exhibiting a noise of less than about 85 dB when subjected to flexing through a 65° angle at 0.45 Hz and having a heat seal strength of at least about 1.0 lb/inch width of said film.

2. The multilayer barrier film of claim 1 wherein said skin layer comprises either a thermoplastic polyurethane, a substantially linear copolymer of ethylene and an α-olefin resin having a density in the range of from about 0.87–0.92 gm/cc and from about 0.01 to 3 long chain branches/1000 carbon atoms along the polymer backbone, a homogeneously-branched linear olefin resin, or a blend of an ultra low density polyolefin resin with a copolymer of ethylene and vinyl acetate.

3. The multilayer barrier film of claim 1 wherein said halogen-free barrier layer is selected from the group consisting of amorphous Nylon, crystalline Nylon, copolymers of ethylene and vinyl alcohol, and blends thereof.

4. The multilayer barrier film of claim 1 including heat sealable skin layers on both surfaces of said halogen-free barrier layer.

5. The multilayer barrier film of claim 1 wherein said skin layer contains from about 0.5–6% by weight of a slip additive/antiblocking agent package.

6. The multilayer barrier film of claim 1 wherein said halogen-free barrier layer comprises an amorphous Nylon resin.

7. The multilayer barrier film of claim 6 wherein said heat sealable skin layer comprises a thermoplastic polyurethane.

8. The multilayer barrier film of claim 7 including an intermediate adhesive tie layer of a chemically modified copolymer of ethylene and vinyl acetate between said barrier layer and said skin layer.

9. The multilayer barrier film of claim 1 wherein said heat sealable skin layer comprises a blend of an ultra low density polyolefin resin with a copolymer of ethylene and vinyl acetate.

10. The multilayer barrier film of claim 9 including an intermediate adhesive tie layer of a copolymer of ethylene and acrylic acid or a chemically modified copolymer of ethylene and vinyl acetate between said barrier layer and said skin layer.

11. The multilayer barrier film of claim 1 wherein said skin layers comprise from about 70–90% by volume of said film and said halogen-free barrier layer comprises from about 10–30% by volume of said film.

12. The multilayer barrier film of claim 1 wherein said film has an oxygen transmission rate of less than about 400 cc/m$^2$/day·atm.

13. The multilayer barrier film of claim 1 wherein said skin layer is a substantially linear copolymer of ethylene and an α-olefin having a density in the range of from about 0.87–0.92 gm/cc, from about 0.01 to 3 long chain branches/1000 carbon atoms along the polymer backbone.

14. The multilayer barrier film of claim 1 wherein said at least one skin layer is heat sealed along its edges to form a bag or pouch.

15. The multilayer barrier film of claim 1 wherein said barrier film further includes:

a) an adhesive containing an active drug adhered to one surface of said barrier film; and b) a controlled release membrane adjacent said adhesive and adapted to controllably release said drug to a patient's skin.

16. The multilayer barrier film of claim 15 further including an adhesive adhered to a least a portion of said controlled release membrane and a release liner overlying said adhesive and release membrane to form a system for transdermal delivery of drugs.

17. An oxygen and moisture impermeable multilayer barrier film comprising a halogen-free polymeric barrier layer and at least one heat sealable skin layer, said skin layer comprising either a thermoplastic polyurethane or a substantially linear copolymer of ethylene and an α-olefin resin having a density in the range of from about 0.87–0.92 gm/cc and from about 0.01 to 3 long chain branches/1000 carbon atoms along the polymer backbone, said skin layer having a 2% secant modulus of less than about 15,000 psi in both the machine and transverse directions, said barrier film exhibiting a noise of less than about 85 dB when subjected to flexing through a 65° angle at 0.45 Hz and having a heat seal strength of at least about 1.0 lb/inch width of said film.

18. The multilayer barrier film of claim 17 in wherein said halogen-free barrier layer is selected from the group consisting of amorphous Nylon, crystalline Nylon, copolymers of ethylene and vinyl alcohol, and blends thereof.

19. The multilayer barrier film of claim 17 including heat sealable skin layers on both surfaces of said halogen-free barrier layer.

20. The multilayer barrier film of claim 17 wherein said skin layer contains from about 0.5–6% by weight of a slip additive/antiblocking agent package.

21. The multilayer barrier film of claim 17 including an intermediate adhesive tie layer of a chemically modified copolymer of ethylene and vinyl acetate between said barrier layer and said skin layer.

22. The multilayer barrier film of claim 17 wherein said skin layers comprise from about 70–90% by volume of said film and said halogen-free barrier layer comprises from about 10–30% by volume of said film.

23. The multilayer barrier film of claim 17 in which said film has an oxygen transmission rate of less than about 400 $cc/m^2/day \cdot atm$.

24. The multilayer barrier film of claim 17 wherein said at least one skin layer is heat sealed along its edges to form a bag or pouch.

25. The multilayer barrier film of claim 17 wherein said barrier film further includes:
   a) an adhesive containing an active drug adhered to one surface of said barrier film; and
   b) a controlled release membrane adjacent said adhesive and adapted to controllably release said drug to a patient's skin.

26. The multilayer barrier film of claim 25 further including an adhesive adhered to at least a portion of said controlled release membrane and a release liner overlying said adhesive and release membrane to form a system for transdermal delivery of drugs.

* * * * *